United States Patent
Atsumi et al.

(10) Patent No.: US 6,544,586 B1
(45) Date of Patent: Apr. 8, 2003

(54) METHOD FOR MANUFACTURING GAS SENSOR ELEMENT

(75) Inventors: Takayoshi Atsumi, Komaki (JP); Koji Shiono, Komaki (JP)

(73) Assignee: NGK Spark Plug Co. Ltd. (JP)

( * ) Notice: Subject to any disclaimer, the term of this patent is extended or adjusted under 35 U.S.C. 154(b) by 0 days.

(21) Appl. No.: 09/249,370

(22) Filed: Feb. 12, 1999

(30) Foreign Application Priority Data

Feb. 16, 1998 (JP) .......................................... 10-033195

(51) Int. Cl.⁷ ................................................ B05D 5/12
(52) U.S. Cl. ............................... 427/126.2; 427/126.3; 427/359; 427/360; 427/201; 427/202; 427/203; 427/428
(58) Field of Search ................................ 427/201, 202, 427/203, 428, 126.2, 126.3, 359, 360; 29/623.4, 623.5; 204/429, 427, 424, 421; 429/41

(56) References Cited

U.S. PATENT DOCUMENTS

| 4,136,000 A | 1/1979 | Davis et al. ................. 204/195 |
| 4,477,487 A | 10/1984 | Kojima et al. ............... 427/123 |
| 4,835,009 A * | 5/1989 | Ishiguro et al. ........... 427/126.2 |
| 4,851,105 A | 7/1989 | Ishiguro et al. ............. 204/429 |
| 4,857,165 A | 8/1989 | Ishiguro et al. ............. 204/424 |
| 5,443,711 A | 8/1995 | Kojima et al. ............... 204/429 |
| 5,681,784 A | 10/1997 | Friese |

FOREIGN PATENT DOCUMENTS

| DE | 4221786 | 1/1994 |
| EP | 0 294 085 | 7/1988 |
| EP | 408039 | 10/1991 |
| JP | 52-54493 | 5/1977 |
| JP | 52-68494 | 6/1977 |
| JP | 53-10491 | 1/1978 |
| JP | 53-85493 | 7/1978 |
| JP | 54-66888 | 5/1979 |
| JP | 58-204365 | 11/1983 |
| JP | 62-198749 | 9/1987 |
| JP | 63-98558 | 4/1988 |
| JP | 63-200055 | 8/1988 |
| JP | 1-132947 | 5/1989 |
| JP | 1-209355 | 8/1989 |
| JP | 05-180797 | 7/1993 |
| JP | 08-109209 | 1/1996 |
| JP | 2598445 | 1/1997 |

* cited by examiner

Primary Examiner—Brian K. Talbot
(74) Attorney, Agent, or Firm—Brinks Hofer Gilson & Lione (57) ABSTRACT

A gas sensor element includes a solid electrolyte layer having a plurality of projections formed on its outer surface, an inner electrode formed on the inner surface of the solid electrolyte layer, an outer electrode formed on the outer surface of the solid electrolyte layer, an outer electrode formed on the outer surface of the solid electrolyte layer and a spinel protection layer formed on the outer electrode for protection. The projections are formed on the outer surface of the solid electrolyte layer such that they are formed in a single layer; an area occupied by the projections accounts for 10% to 85% of the outer surface of the solid electrolyte layer and the distance between the neighboring projections is 5 $\mu$m to 300 $\mu$m. Thus, the outer electrode is formed on the solid electrolyte layer in such a manner as to penetrate into pits formed between neighboring projections and is thus strongly bonded to the solid electrolyte layer, thereby improving thermal durability. Also, since pores are hardly formed or are not formed at all between projections, a strong bond is established among the solid electrolyte layer, the outer electrode, and the protection layer, thereby improving durability against high temperature and high humidity.

18 Claims, 7 Drawing Sheets

BEFORE AUTOCLAVE TEST
FOR DURABILITY

FIG. 5A

DURING AUTOCLAVE TEST
FOR DURABILITY--PART 1

FIG. 5B

DURING AUTOCLAVE TEST
FOR DURABILITY--PART 2

FIG. 5C

AFTER AUTOCLAVE TEST FOR DURABILITY (BREAKAWAY OF
PROJECTIONS AND CRACKING IN SPINEL LAYER)

METHOD FOR MANUFACTURING GAS SENSOR ELEMENT

BACKGROUND OF THE INVENTION

1. Field of the Invention

The present invention relates to a gas sensor element which includes a solid electrolyte layer having a plurality of projections on its outer surface, an inner electrode provided on the inner surface of the solid electrolyte layer, an outer electrode provided on the outer surface of the solid electrolyte layer and a protection layer covering the outer electrode for protection of the outer electrode and in which an electrical characteristic value as measured between the electrodes varies according to a component of gas to be detected.

2. Description of Related Art

Conventionally, there is known a structure of and a manufacturing method for an oxygen concentration cell which exhibits such excellent heat resistance that an electrode does not come off even when the cell is exposed to a high-temperature environment for a long period of time. The manufacturing method comprises the steps of: applying a mixture of granules and minute particles onto the surface of a zirconia base body; and firing the base body and the applied mixture simultaneously to thereby form a number of pits and projections on the surface of the base body.

For example, Japanese Patent Application Laid-Open (kokai) No. 56-160653 discloses a method for manufacturing a zirconia oxygen sensor element, including a step of applying a paste of mixed granules and minute particles onto a surface of a zirconia base body at a thickness of 40 μm to 300 μm through use of a brush. According to the publication, projections are formed on the surface of the base body through firing, and the surface is coated with an electrode. As a result, the electrode penetrates into pits formed between projections, thereby increasing its surface area and establishing a strong bond. Also, Japanese Patent Publication No. 2-44391 discloses a method for manufacturing a zirconia oxygen sensor element, including a step of applying a similar paste onto a surface of a zirconia base body in an overflowing manner through use of a roller so as to form a surface layer having a final thickness of 100 μm.

In recent years, an oxygen concentration cell has often been required to be installed downstream of a three-way catalytic converter. Thus, the oxygen concentration cell must function properly in an environment having a temperature of 200° C. to 300° C. and that is rich with water vapor in which zirconia is apt to undergo phase transition.

However, the oxygen sensor elements described in Japanese Patent Application Laid-Open (kokai) No. 56-160653 and Japanese Patent Publication No. 2-44391 include portions where granules are present in layers, implying the formation of pores. A "pore" is a minute opening formed between neighboring projections as a result of bonding of tips of the projections or between layered projections. Thus, water vapor enters the pores, causing the phase transition of zirconia to extend to considerably deep portions of projections.

Accordingly, the projections change in volume on a microscopic scale, causing the formation of minute cracks in the projections. Therefore, the projections may break away from the zirconia base body to cause a crack failure.

SUMMARY OF THE INVENTION

A gas sensor element includes a solid electrolyte layer having a plurality of projections formed on its outer surface, an inner electrode formed on the inner surface of the solid electrolyte layer, an outer electrode formed on the outer surface of the solid electrolyte layer, an outer electrode formed on the outer surface of the solid electrolyte layer and a spinel protection layer formed on the outer electrode for protection. The projections are formed on the outer surface of the solid electrolyte layer such that they are formed in a single layer; an area occupied by the projections accounts for 10% to 85% of the outer surface of the solid electrolyte layer and the distance between the neighboring projections is 5 μm to 300 μm.

Thus, the outer electrode is formed on the solid electrolyte layer in such a manner as to penetrate into pits formed between neighboring projections and is thus strongly bonded to the solid electrolyte layer, thereby improving thermal durability. Also, since pores are hardly formed or are not formed at all between projections, a strong bond is established among the solid electrolyte layer, the outer electrode, and the protection layer, thereby improving durability against high temperature and high humidity.

In view of the foregoing, an object of the present invention is to provide a gas sensor element exhibiting improved durability against high temperature and high humidity while maintaining a strong bond between a solid electrolyte layer and an outer electrode and a strong bond between the outer electrode and a protection layer, as well as to provide a method for manufacturing the gas sensor element.

BRIEF DESCRIPTION OF THE DRAWINGS

FIG. 1 presents views explaining an overflow coating applicator, wherein

FIG. 3 presents views explaining a generation mechanism of pores in overflow coating, wherein

FIG. 4 presents views explaining variations in projections during the autoclave test for durability of Test Example 2, wherein

FIG. 5 presents views explaining variations in projections during the autoclave test for durability of Test Example 4, wherein

DESCRIPTION OF THE PREFERRED EMBODIMENT

In order to solve the above problems, according to a first aspect of the present invention, there is provided a gas sensor element comprising a solid electrolyte layer having a plurality of projections on its outer surface, an inner electrode provided on an inner surface of the solid electrolyte layer, an outer electrode provided on an outer surface of the solid electrolyte layer, and a protection layer covering the outer electrode for protection of the outer electrode. An electrical characteristic value as measured between the electrodes varies according to a component of gas to be detected.

The gas sensor element is characterized in the following: a plurality of projections are formed on a portion of or on the entirety of a region of the outer surface of the solid electrolyte layer that is covered with the protection layer; the plurality of projections are formed in a single layer; an area occupied by the projections accounts for 10% to 85% that of the portion of the outer surface of the solid electrolyte layer on which the projections are formed; and the distance between the neighboring projections is 5 $\mu$m to 400 $\mu$m.

Figure 7:
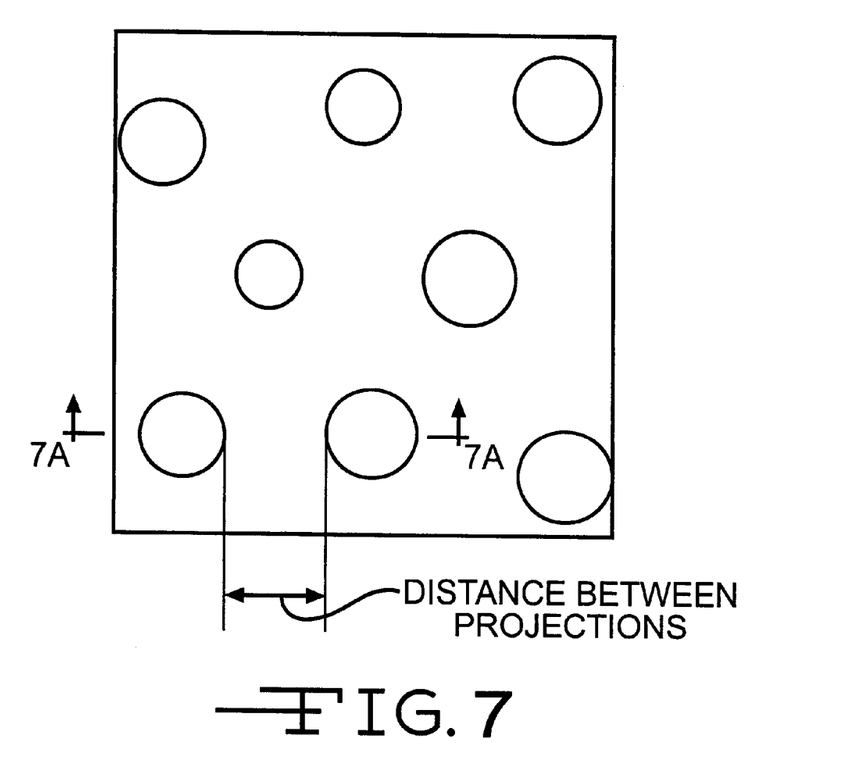
FIG. 7 is a schematic view representing a scanning electron microscope photo of the outer surface of a solid electrolyte layer.
Figure 7A:
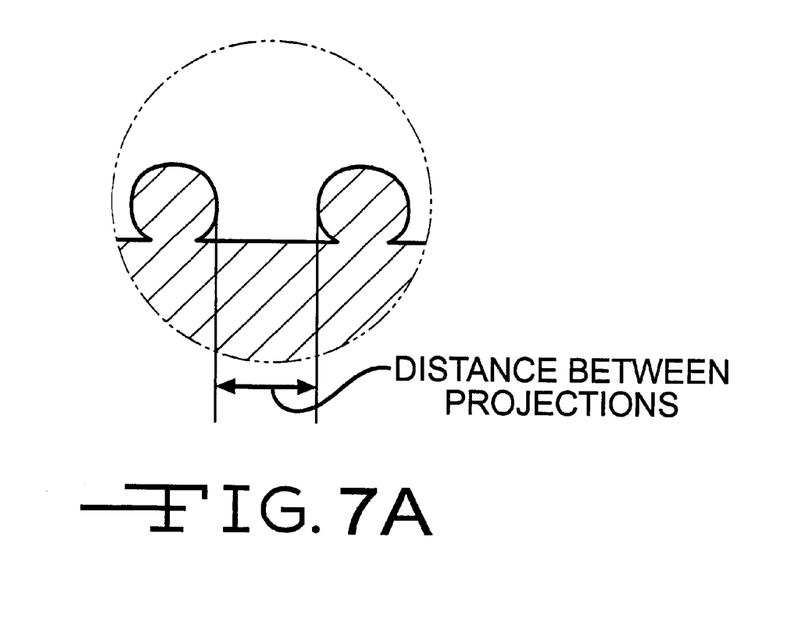

As one means to confirm that a plurality of projections are formed on a portion of or on the entirety of a region of the outer surface of the solid electrolyte layer that is covered with the protection layer and that the above characteristic conditions are met, the outer surface of the solid electrolyte layer is photographed through a scanning electron microscope (SEM), and the thus-photographed surface is examined (see FIG. 7). The distance between projections refers to a gap between the surfaces of neighboring projections (see sectional view taken along line A—A in FIG. 7).

In the gas sensor element, if the area occupied by projections accounts for less than 10% of the portion of the outer surface of the solid electrolyte layer on which the projections are formed or if the distance between projections is in excess of 400 $\mu$m, even when the outer electrode is formed on the solid electrolyte layer in such a manner as to penetrate into pits between projections, the bond between the outer electrode and the solid electrolyte layer becomes weak. By contrast, if the area occupied by projections accounts for greater than 85% that of the portion of the outer surface of the solid electrolyte layer on which the projections are formed or if the distance between projections is less than 5 $\mu$m, pores are apt to be formed between layered projections or between neighboring projections. Water vapor, when entering the pores, causes the phase transition of zirconia to extend to considerably deep portions of projections. Accordingly, the projections change in volume on a microscopic scale, causing the formation of minute cracks in the projections. Therefore, the projections may break away from the zirconia base body to cause a crack failure. Particularly preferably, the area occupied by projections accounts for not greater than 75% that of the portion of the outer surface of the solid electrolyte layer on which the projections are formed, and the distance between projections is not less than 30 $\mu$m.

In the gas sensor element, the outer electrode is formed on the solid electrolyte layer in such a manner as to penetrate into pits formed between neighboring projections and is thus strongly bonded to the solid electrolyte layer. Thus, the outer electrode and the protection layer are free from coming-off, thereby improving thermal durability. Also, since pores are hardly formed or are not formed at all, even when the gas sensor element is exposed to high temperature (for example, 200° C. to 300° C.) in the presence of rich water vapor, the phase transition of zirconia does not extend to considerably deep portions of projections. Therefore, the projections do not break away from the outer surface of the solid electrolyte layer.

As described above, the gas sensor element according to the first aspect yields the effect of improving durability against high temperature and high humidity while maintaining a strong bond between the sold electrolyte layer and the outer electrode and a strong bond between the outer electrode and the protection layer. The gas sensor element yields the effect even when projections are formed on a portion of the region of the outer surface of the solid electrolyte layer that is covered with the protection layer. Preferably, projections are formed on the entirety of the region of the outer surface of the solid electrolyte layer that is covered with the protection layer, since the yielded effect is more noticeable.

According to a second aspect of the present invention, there is provided a method for manufacturing a gas sensor element comprising the steps of: rotating a substantially cylindrical base body made of an unfired solid electrolyte material, applying a paste—which includes roughening particles of material substantially similar to that for the base body and has a viscosity of 500 CPS to 1600 CPS—onto the base body in such a manner that the paste is brought into contact with the base body and is moved in a direction opposite to a moving direction of the base body at a position of contact between the paste and the base body and firing the base body coated with the paste to thereby form a plurality of projections on the base body.

In the method for manufacturing a gas sensor element, the solid electrolyte material may contain as a main component stabilized or partially stabilized zirconia, for example, and, as needed, $Al_2O_3$, $SiO_2$, and $Fe_2O_3$. The base body may be prepared by the steps of: mixing $ZrO_2$ with a bivalent or trivalent metallic oxide, such as $Y_2O_3$, CaO, or MgO, in a desired proportion and pulverizing the resultant mixture; preliminarily firing the mixture in an electric furnace; pulverizing the preliminarily fired mixture to thereby obtain a material powder of stabilized or partially stabilized zirconia; and forming the material powder into a substantially cylindrical shape; for example, into a cylinder with one closed end, by way of a pressing method, such as a rubber press method, or by way of a laminating method, such as a thick-film method. The paste is a fluidized mixture, which includes roughening particles of material substantially similar to that for the base body. Material for the roughening particles is not necessarily identical to that for the base body, but must be basically identical in properties to that for the base body. Otherwise, in the subsequent firing process, the base body and the roughening particles may not be integrated stably and reliably. The base body coated with the paste is dried and is then fired at a temperature of 1400° C. to 1600° C. for 1 to 3 hours, for example. An oxidizing atmosphere is usually preferred for firing.

The base body having a plurality of projections formed thereon through firing serves as the solid electrolyte layer having a plurality of projections on its outer surface. An electrode is formed on each of the inner and outer surfaces of the solid electrolyte layer. Usually, a heat resistant, catalytic metal is used as material for the electrodes. Examples of such a metal include platinum, ruthenium, rhodium, palladium, and their alloys. Examples of the method for forming the electrodes include vacuum deposition, chemical deposition, electroless plating, electroplating, and a method composed of the steps of applying a decomposable metal salt onto the solid electrolyte layer and heating the coated solid electrolyte layer so as to deposit the metal through decomposition. The outer electrode is formed along the rugged surface of the solid electrolyte layer, thereby increasing the surface area of the electrode and improving adhesion of the electrode.

According to the method for manufacturing a gas sensor element, the paste is moved in a direction opposite to a moving direction of the base body at the position of contact between the paste and the base body, thereby substantially uniformly applying the paste onto the outer surface of the rotating base body and thus substantially uniformly distributing roughening particles throughout the outer surface of the base body. This method for manufacturing a gas sensor element is suited for applying roughening particles in such a manner as to meet the following conditions: a plurality of projections are formed on a portion of or on the entirety of the region of the outer surface of the solid electrolyte layer that is covered with the protection layer; the plurality of projections are formed in a single layer; an area occupied by the projections accounts for 10% to 85% that of the portion of the outer surface of the solid electrolyte layer on which the projections are formed; and the distance between neighboring projections is 5 $\mu$m to 400 $\mu$m. Thus, the method is suited for manufacture of the gas sensor element according to the first aspect of the invention.

Preferably, the paste is fed onto the outer circumferential surface of a rotary drum rotating in the same direction as does the base body, such that the fed paste is present in a predetermined thickness on the drum. In this case, through employment of a simple apparatus configuration, the paste and the base body can be moved in opposite directions at the position of contact between the paste and the base body. Preferably, in view of manufacture of the gas sensor element according to the first aspect of the invention, the axial rotational speed of the base body and the rotational speed of the rotary drum are regulated such that the base body is moved at a speed of 3.0 cm/sec to 24.0 cm/sec at the contact position and such that the paste is moved at a speed of 2.0 cm/sec to 8.0 cm/sec at the contact position. If the base body is moved at a speed of less than 3.0 cm/sec, the amount of the paste adhering to the base body increases. Consequently, pores are more apt to be formed. If the base body is moved at a speed in excess of 24.0 cm/sec, the friction between the base body and the roughening particles contained in the paste tends to initiate wear on the base body. If the paste is moved at a speed of less than 2.0 cm/sec, the paste present on the rotary drum tends to flow downward due to its own weight. If the paste is moved at a speed in excess of 8.0 cm/sec, the amount of the paste adhering to the base body increases. Consequently, pores are more apt to be formed.

Preferably, in view of manufacture of the gas sensor element according to the first aspect of the invention, the weight of the paste adhering to the base body is 5.0 mg/cm$^2$ to 18.0 mg/cm$^2$. If the weight of the paste adhering to the base body is less than 5.0 mg/cm$^2$, formation of a sufficient number of projections on the surface of the base body becomes difficult to achieve; consequently, thermal durability may not be improved sufficiently. If the weight of the paste adhering to the base body is in excess of 18.0 mg/cm$^2$, pores are apt to be formed.

Preferably, in view of manufacture of the gas sensor element according to the first aspect of the invention, the paste contains granules having a grain size of 20 $\mu$m to 100 $\mu$m and minute particles having a grain size smaller than that of the granules. A mixture of the granules and the minute particles serves as roughening particles. If the grain size of granules is less than 20 $\mu$m. formation of a number of projections having good heat resistance on the surface of the base body becomes difficult, which is similar to the case of formation of an unfavorable porous layer. If the grain size of granules is in excess of 100 $\mu$m, the granules themselves tend to fail in achieving a strong bond with the base body.

A method for forming such favorable granules is not particularly limited, but granulation through use of a spray drier stabilizes the shape of granules and produces fine granules. The thus-produced granules exhibit an increased bonding force with the base body. Therefore, employment of a spray drier for granulation is preferred. According to granulation through use of a spray drier, a material powder mixed with an appropriate organic binder undergoes an ordinary wet method. The minute particles to be used are usually such that most of the minute particles have a grain size of not greater than 10 $\mu$m, preferably such that at least 80% of the minute particles have a grain size of not greater than 2.5 $\mu$m. Since the minute particles are used as sintering aids for aiding formation of a bond between the base body and the granules, particles having a relatively large grain size cannot sufficiently yield the required aiding effect. Preferably, in view of manufacture of the gas sensor element according to the first aspect of the invention, the paste contains the granules and the minute particles in a mixing ratio of 80:20 to 20:80. If the ratio of the granules to the fine particles is in excess of 80:20, the granules tend to fail in achieving a strong bond with the surface of the base body. If the ratio of the granules to the minute particles is less than 20:80, formation of a sufficient number of projections on the surface of the base body becomes difficult and thus thermal durability may not be sufficiently improved.

Preferably, in view of manufacture of the gas sensor element according to the first aspect of the invention, the paste has a viscosity of 500 CPS to 1600 CPS, particularly 500 CPS to 1000 CPS. If the viscosity is less than 500 CPS, granules contained in the paste precipitate quickly; consequently, uniform formation of projections throughout the surface of the base body tends to become difficult. If the viscosity is in excess of 1600 CPS, projections tend to be formed in layers on the base body. In order to reliably prevent projections from being formed in layers on the base body, the upper limit of the viscosity is preferably set to 1000 CPS.

Notably, an optimum paste for use in the method for manufacturing a gas sensor element according to the second aspect of the invention meets the following conditions: a mixed solvent of water and an organic binder contains granules and minute particles in a mixing ratio of 80:20 to 20:80—the granules have a grain size of 20 $\mu$m to 100 $\mu$m, and the fine particles are usually such that most of the minute particles have a grain size of not greater than 10 $\mu$m, preferably such that at least 80% of the minute particles have a grain size of not greater than 2.5 $\mu$m; viscosity is 500 CPS to 1000 CPS; and the paste applied onto the base body has a thickness of 20 $\mu$m to 200 $\mu$m. The mixed solvent preferably contains water and an organic binder in a mixing ratio of 200:1 to 20:1. Examples of such an organic binder include Na-CMC (sodium cellulose glycolate), NH$_4$-CMC (ammonium cellulose glycolate), and PVA (polyvinyl alcohol). The mixing ratio of water and an organic binder greatly influences the viscosity of the paste. For example, in the case of using NH$_4$-CMC, if the ratio of water to NH$_4$-CMC is in excess of 200:1, the viscosity of the paste decreases, and thus granules contained in the paste precipitate quickly; consequently, uniform formation of projections throughout the surface of the base body tends to become difficult. If the ratio of water to NH$_4$-CMC is less than 20:1, the viscosity of the paste increases; consequently, projections tend to be formed in layers on the base body. Further, after firing, binder portions tend to result in formation of pores.

TABLE 1

| Test Examples | 1 | 2 | 3 | 4 | 5 | 6 |
|---|---|---|---|---|---|---|
| Paste | | | | | | |
| Fine particles (g) | 910 | 455 | 455 | 910 | 455 | 455 |
| Preliminarily fired granules (g) | 490 | 245 | 245 | 490 | 245 | 245 |
| Binder (g) | 27 | 23 | 23 | 27 | 23 | 23 |
| Water (g) | 1800 | 1800 | 2800 | 1800 | 1800 | 2800 |
| Viscosity (CPS) | 1600 | 850 | 400 | 1600 | 850 | 400 |
| Rotational directions of base and drum | Same | Same | Same | Opposite | Opposite | Opposite |
| Areal percentage of projections in 500 × 500 $\mu$m visual field (%) | 70–80 | 50–70 | ≦10 | ≧90 | 60–85 | ≦10 |
| Distance between projections ($\mu$m) | 20–30 | 50–280 | ≧400 | 0–10 | 5–270 | ≧400 |
| Autoclave test for durability (200° C.) | | | | | | |
| 3 hr. | ○ | ○ | ○ | ○ | ○ | ○ |
| 6 hr. | ○ | ○ | ○ | x | ○ | ○ |
| 9 hr. | ○ | ○ | ○ | x | ○ | ○ |
| 12 hr. | x | ○ | ○ | x | x | ○ |
| Thermal durability (cycles) | 850 | ≧1000 | 280 | 430 | 850 | 280 |
| Overall evaluation | BBB | AAA | XXX | XXX | BBB | XXX |

AAA: excellent;
BBB: good;
XXX: poor

As to Test Example 1, 6 Mol % yttrium oxide was added to zirconium oxide. The resultant mixture was wet pulverized for 70 hours. The pulverized mixture was dried and was then put through a 20-mesh sieve. The obtained particles were preliminarily fired at 1300° C. for 1 hour in an electric furnace. The fired particles were put through a 20-mesh sieve. Then, the obtained particles were wet pulverized for 50 hours through use of a ball mill, obtaining material powder in which particles having a grain size of not greater than 2.5 $\mu$m account for 90% of the entire material powder. Gum arabic serving as an organic binder was added to the material powder, obtaining slurry. The obtained slurry was processed through use of a spray drier, yielding granules having an average grain size of about 60 $\mu$m. The water content of the granules was adjusted to 1%. The granules were then formed into a base body having a cylindrical shape with one closed end (i.e., a cup shape, or a closed-bottomed cylindrical shape) through use of a 50 Pa rubber press. This base body includes a sensing portion (a portion covered with a spinel protection layer, which will be described later) having an average diameter of 6.5 mm and an outer surface area of about 5.7 cm$^2$.

The above granules obtained by processing through use of the spray drier were preliminarily fired at a temperature of 1200° C. to 1300° C. for 1 hour, followed by sieving to obtain granules having a grain size of 60 $\mu$m to 100 $\mu$m. The thus-obtained granules and the fine particles at least 80% of which have a grain size of not greater than 2.5 $\mu$m were added in ratios as shown in Table 1 to a mixed solvent of water and water-soluble binder NH$_4$-CMC, yielding a paste having a viscosity of 400 CPS to 1600 CPS.

Figure 1A:
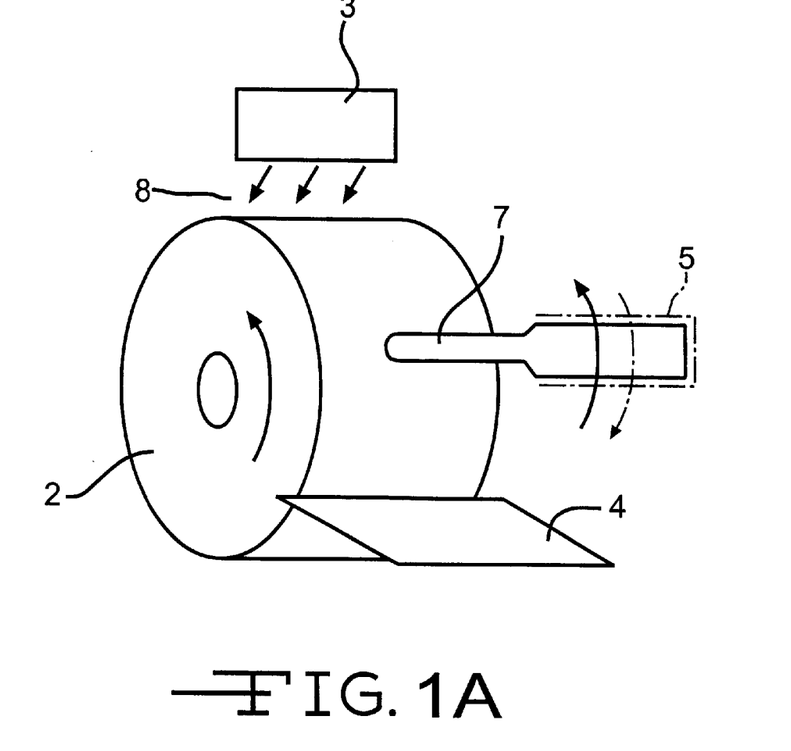
FIG. 1(a) is a schematic perspective view.
Figure 1B:
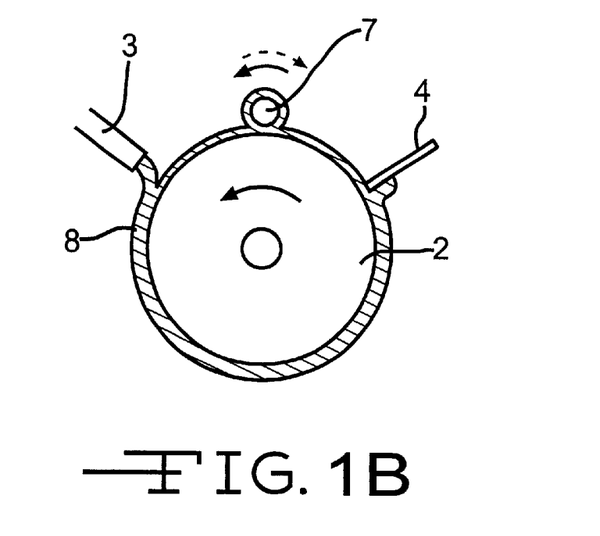
FIG. 1(b) is a schematic sectional view.

This paste was applied onto a portion (sensing portion) of the outer surface of the above unfired base body, which portion is to be covered with a spinel protection layer (described later), through overflow coating by means of a roller. The base body coated with the paste was fired at 1600° C. for 1 hour in an oxidizing atmosphere. As shown in FIG. 1, an overflow coating applicator 1 includes a rotary drum 2 (diameter: 90 mm), a paste feeder 3, a plate 4, and a rotary base-body support 5. The rotary drum 2 is adapted to apply the paste onto the unfired base body. The paste feeder 3 feeds the paste onto the outer circumferential surface of the rotary drum 2. The plate 4 is adapted to scrape off the paste such that the thickness of the paste applied onto the outer circumferential surface of the rotary drum 2 becomes constant (herein, 300 $\mu$m). The rotary base-body support 5 is adapted to support the unfired base body such that the unfired base body can rotate about its axis and comes into contact with the paste applied onto the outer circumferential surface of the rotary drum 2. The rotary base-body support 5 can switch directions of its rotation. As shown in Table 1, the direction of rotation of the rotary base-body support 5 was set identical to or opposite to that of the rotary drum 2 for individual Test Examples. The overflow coating applicator 1 was adjusted such that the rotational speed of the drum became 10 rpm (the speed of the paste became 4.8 cm/sec at a position of contact between the paste and the base body), and the rotational speed of the rotary base-body support 5 became 300 rpm (the speed of the base body became 10.2 cm/sec at the position of contact between the paste and the base body). A tip portion (bottom portion) of the base body is coated with the paste through the rising effect of the paste.

Figure 2:
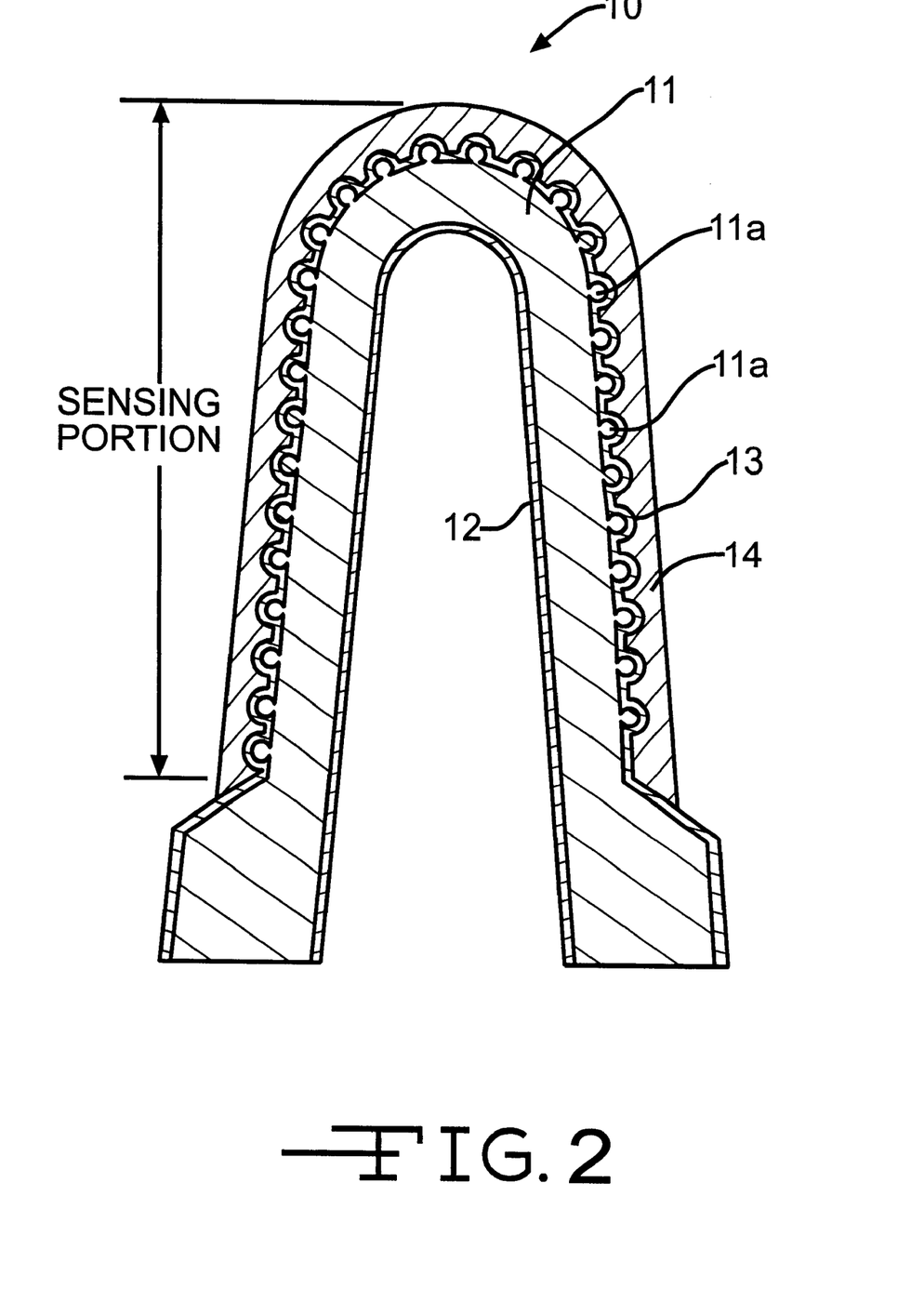
FIG. 2 is as schematic sectional view of a gas sensor element according to the present invention.

After the base body was fired (the fired base body is referred to as a solid electrolyte layer), a platinum electrode was formed on the inner and outer surfaces of the solid electrolyte layer by way of a known plating method. Further, a spinel protection layer was formed on the outer electrode by way of a known plasmatic thermal spraying method, thereby obtaining a gas sensor element as shown in FIG. 2. A gas sensor element 10 includes a solid electrolyte layer 11 having a plurality of projections on its outer surface; an inner electrode 12 provided on the inner surface of the solid electrolyte layer 11; an outer electrode 13 provided on the outer surface of the solid electrolyte layer 11; and a spinel protection layer covering the outer electrode 13 for protection of the outer electrode 13. An electrical characteristic value as measured between the electrodes 12 and 13 varies according to a component of gas to be detected.

Test Examples 1 and 4, Test Examples 2 and 5, and Test Examples 3 and 6 respectively used pastes having the same composition. In Test Examples 1, 2 and 3, the base body and the drum were rotated in the same direction (i.e., the paste and the base body were moved in opposite directions), whereas in Test Examples 4, 5 and 6, the base and the drum were rotated in opposite directions (i.e., the paste and the base body were moved in the same direction).

The thus-obtained gas sensor elements of Test Examples 1 through 6 were examined in the following manner. The spinel protection layer was removed, and then the outer electrode was eluted into aqua regia. Subsequently, the outer surface of the solid electrolyte layer was photographed through an SEM and with respect to a square visual field of 500 $\mu$m by 500 $\mu$m. The thus-obtained photos were examined for an areal percentage of projections to the area of the visual field and the distance between neighboring projections. Table 1 shows the results of the examination. Sections of the gas sensor elements were also photographed through an SEM. The thus-obtained photos were examined for pores. In the gas sensor elements other than that of Test Example 4, projections were formed in a single layer, and pores were hardly formed or were not formed at all. By contrast, in the gas sensor element of Test Example 4, projections were formed in layers, and pores were considerably formed.

Figure 3A:
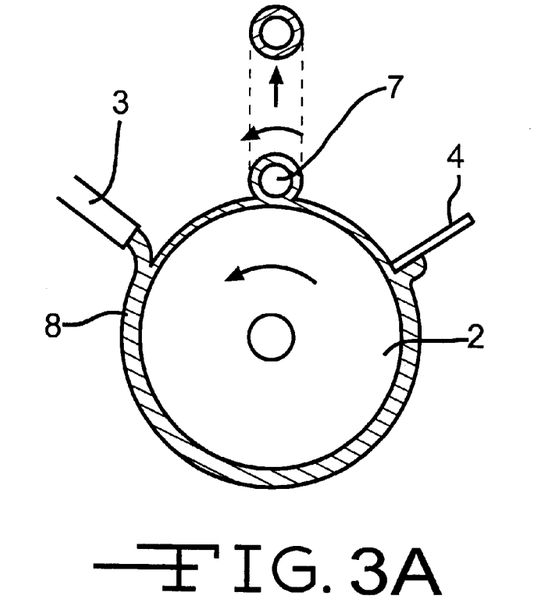
FIG. 3(a) is a view associated with Test Example 1.
Figure 3B:
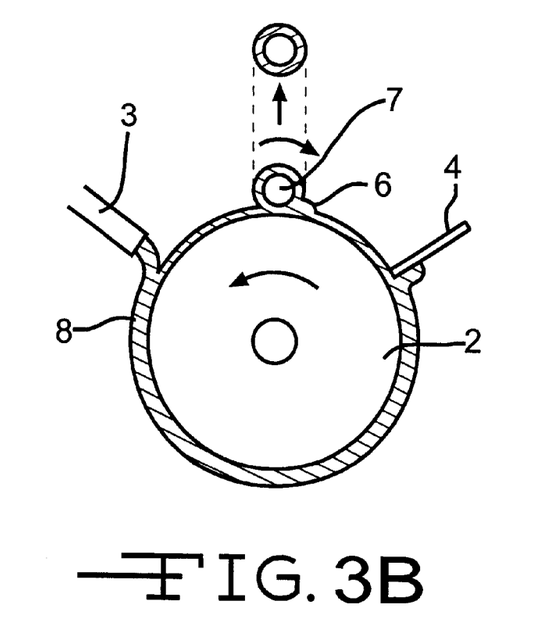
FIG. 3(b) is a view associated with Test Example 4.
Figure 4A:
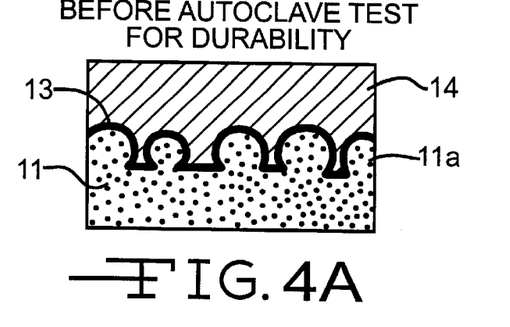
FIG. 4(a) is before the autoclave test.
Figure 4B:
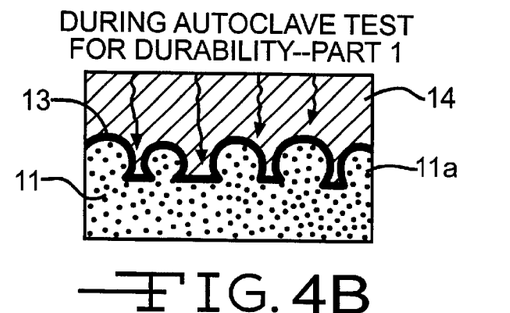
FIG. 4(b) is during part one of the autoclave test.
Figure 4C:
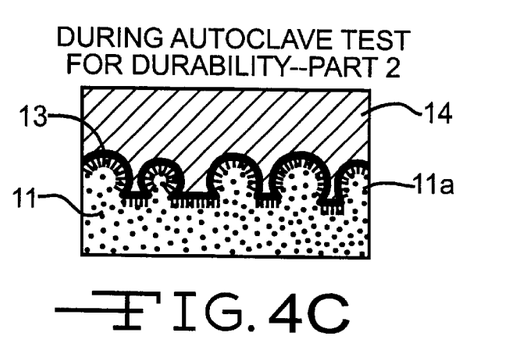
FIG. 4(c) is during part two of the autoclave test and FIG. 4(d) is after the autoclave test.
Figure 4D:
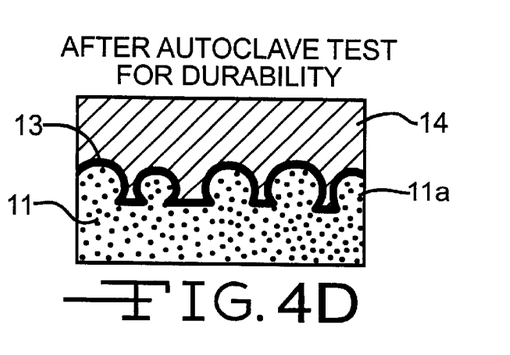
Figure 5A:
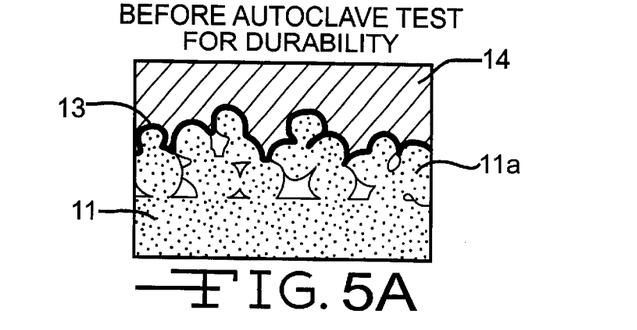
FIG. 5(a) is before the autoclave test.
Figure 5B:
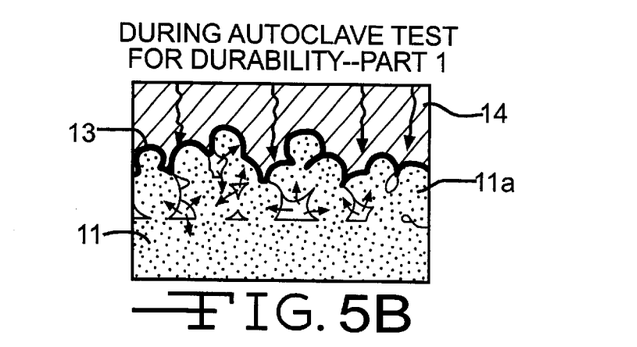
FIG. 5(b) is during part one of the autoclave test.
Figure 5C:
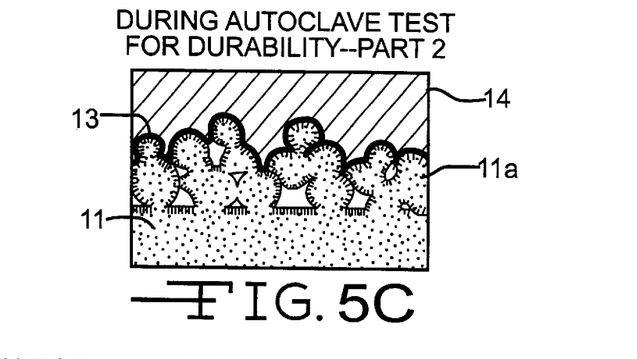
FIG. 5(c) is during part two of the autoclave test and FIG. 5(d) is after the autoclave test showing the break away of projections and cracking in the spinel layer.
Figure 5D:
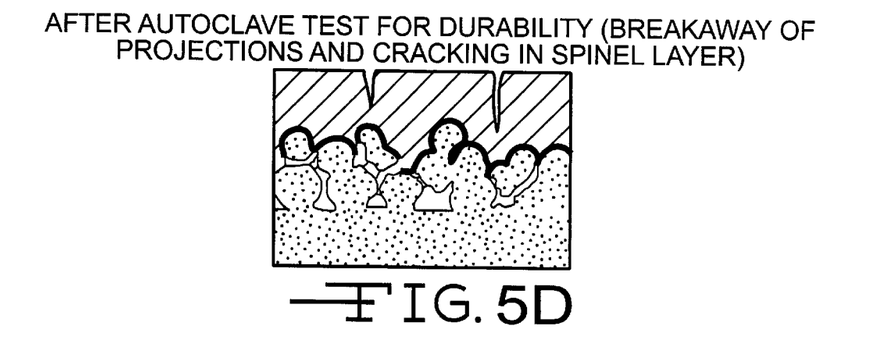

Comparing Test Example 1 and Test Example 4, in Test Example 1 the base body and the drum rotated in the same direction, whereas in Test Example 4 the base body and the drum rotated in opposite directions. Test Examples 1 and 4 were identical in other conditions. In Test Example 1 pores were hardly formed or are not formed at all, whereas in Test Example 4 pores were considerably formed. This resulted from the following. In Test Example 1, as shown in FIG. 3($a$), while the paste was being applied onto the unfired base body by the overflow coating applicator 1, the paste did not stagnate at the position of contact between the base body and the paste present on the drum 2. Accordingly, when the base body was raised, the paste uniformly adhered to the outer surface of the base body. By contrast, in Test Example 4, as shown in FIG. 3($b$), during overflow coating, the paste stagnated at the position of contact between the base body and the paste present on the drum 2. As a result, when the base body was raised, the paste did not uniformly adhere to the outer surface of the base body, causing formation of a coated portion where projections were arranged in layers. In such a coated portion, many pores were formed.

Also, the gas sensor elements of Test Examples 1 to 6 were left within an autoclave which contained saturated water vapor at a temperature of 200° C.(autoclave test for durability). The gas sensor element of Test Example 4 became defective after the elapse of 6 hours. By contrast, in Test Examples 1 and 5, it was not until 12 hours later that the gas sensor elements became defective. In Test Examples 2, 3, and 6, the gas sensor elements were still sound even after the elapse of 12 hours. In Test Example 4, conceivably, water vapor penetrated into pores formed between projections of the solid electrolyte layer; consequently, the phase transition of zirconia extended to considerably deep portions of projections. As a result, at a relatively early stage, the projections changed in volume on a microscopic scale, causing the formation of minute cracks in the projections. Hence, the gas sensor element of Test Example 4 became defective.

In Test Examples other than Test Example 4, conceivably, pores were hardly formed or were not formed at all between projections; thus, sound durability was maintained under autoclave test conditions. In Test Examples 1 and 5, conceivably, pores were slightly formed between projections, or the distance between neighboring projections was shorter than that in the case of Test Examples 2, 3, and 6; consequently, the gas sensor elements became defective slightly earlier than in the case of Test Examples 2, 3, and 6. Notably, the term "defective" refers to a case in which, after exposure to saturated water vapor having a temperature of 200° C. for a predetermined period of time, an appearance defect; for example, coming-off or cracking of the spinel layer is observed, or in which the breakaway of a projection (s) from the base body is found in observation of a section of the gas sensor element through an SEM. The term "sound" refers to a case in which such anomalies are not observed.

The mechanism of durability under autoclave test conditions will next be described with reference to FIGS. 4 and 5 associated with Test Example 2 (model of best durability) and Test Example 4 (model of poor durability), respectively. In FIGS. 4 and 5, the arrow "←" indicates penetration of water vapor, and the shade "///" indicates a phase-transited layer of zirconia. In the case of Test Example 2, durability was conceivably held intact in the following manner. During the autoclave test for durability as shown in FIG. 4, water vapor penetrated into the spinel protection layer 14 and reached the solid electrolyte layer 11 (see FIG. 4($b$)). However, since water vapor could attack only the surface of the solid electrolyte layer 11 (see FIG. 4($c$)), projections 11$a$ did not break away and were maintained in a sound state (see FIG. 4($d$)).

By contrast, in the case of Test Example 4, durability was conceivably impaired in the following manner. During the autoclave test for durability as shown in FIG. 5, water vapor reached considerably deep portions of the projections 11$a$ (see FIG. 5($b$)), since pores were formed between the projections 11$a$ present in layers. Thus, water vapor attacked the projections 11$a$ from every direction. The thus-attacked zirconia suffered the progress of phase transition (see FIG. 5($c$)). As a result, the projections 11$a$ broke away (see FIG. 5($d$)). The breakaway of the projection 11$a$ starts at its relatively weak portion, resulting from a failure to endure a change in volume caused by the phase transition. When the breakaway of the projections 11$a$ is significant, the spinel protection layer 14 may crack.

Also, the gas sensor elements of Test Examples 1 through 6 were tested for thermal durability. A process of leaving the gas sensor elements exposed to heat having a temperature of 1000° C. for 5 minutes and then allowing them to stand at the room temperature was defined as 1 cycle. The gas sensor elements were examined for the number of cycles (thermal durability) until the spinel protection layer came off. The results were as follows: 280 cycles for Test Examples 3 and 6; 430 cycles for Test Example 4; 850 cycles for Test Examples 1 and 5; and not less than 1000 cycles for Test Example 2. In Test Examples 3 and 6, the outer electrode was formed in such a manner as to penetrate into pits formed between projections. However, since the distance between projections is relatively large, a strong bond was not established between the solid electrolyte layer and the outer electrode and between the outer electrode and the spinel protection layer. This is a conceivable reason why the spinel protection layer came off in a relatively small number of cycles.

In Test Example 4, projections having favorable heat resistance were not formed in sufficient quantity on the surface of the solid electrolyte layer. This is equivalent to a state in which a porous layer is formed. As a result, a strong bond was not established between the solid electrolyte layer and the outer electrode and between the outer electrode and the spinel protection layer. This is a conceivable reason whey the spinel protection layer came off in a relatively small number of cycles.

By contrast, in Test Examples 1, 2, and 5, a number of projections having favorable heat resistance were formed on the surface of the solid electrolyte layer while an appropriate distance was maintained between projections. Thus, the outer electrode was formed in such a manner as to penetrate into pits formed between projections. Also, a strong bond was established between the solid electrolyte layer and the outer electrode and between the outer electrode and the spinel protection layer. This is a conceivable reason why the spinel protection layer did not easily come off.

As described above, the gas sensor elements of Test Examples 1, 2, and 5 exhibit improved durability against high temperature and high humidity, while maintaining a strong bond between the solid electrolyte layer and the outer electrode and a strong bond between the outer electrode and the protection layer. The gas sensor elements of Test Examples 1, 2, and 5 are embodiments of the present invention. Particularly, the gas sensor element of Test Example 2 exhibits the best performance. The method for manufacturing the gas sensor elements of Test Examples 1 and 2 is the method for manufacturing a gas sensor element according to the present invention.

The relationship among rotational speed of the drum 2, rotational speed of the base body, and the weight of adhering paste will now be described with reference to FIG. 6. Through use of the above overflow coating applicator (drum diameter: 90 mm; base body diameter: 6.5 mm) and the paste of Test Example 2, how the weight of paste adhering to the base body varies with the rotational speed of the drum and with the rotational speed of the base body was examined. At a weight of adhering paste of 30 mg to 100 mg (represented by the shaded area of FIG. 6; equivalent weight per unit area: about 5.0 to 18.0 mg/cm$^2$), pores were hardly formed or were not formed at all; durability under autoclave test conditions was improved; and a number of projections were formed at appropriate intervals on the surface of the base body, thereby exhibiting improved thermal durability against coming off of the spinel protection layer and of the outer electrode.

At a rotational speed of the drum of less than 5 rpm, the paste present on the rotary drum ran downward due to its own weight. At a rotational speed of the drum in excess of 15 rpm, the weight of paste adhering to the base body tended to vary greatly with the rotational speed of the base body. Thus, uniform application of the paste onto the outer surface of the base body tended to become difficult to achieve.

At a rotational speed of the base body in excess of 700 rpm, significant friction between the base body and granules contained in the paste caused scratches on the base body and thus caused the base body to wear. At a rotational speed of the base body of less than 100 rpm, the weight of paste adhering to the base body tended to vary greatly with the rotational speed of the drum. Thus, uniform application of the paste onto the outer surface of the base body tended to become difficult to achieve.

Figure 6:
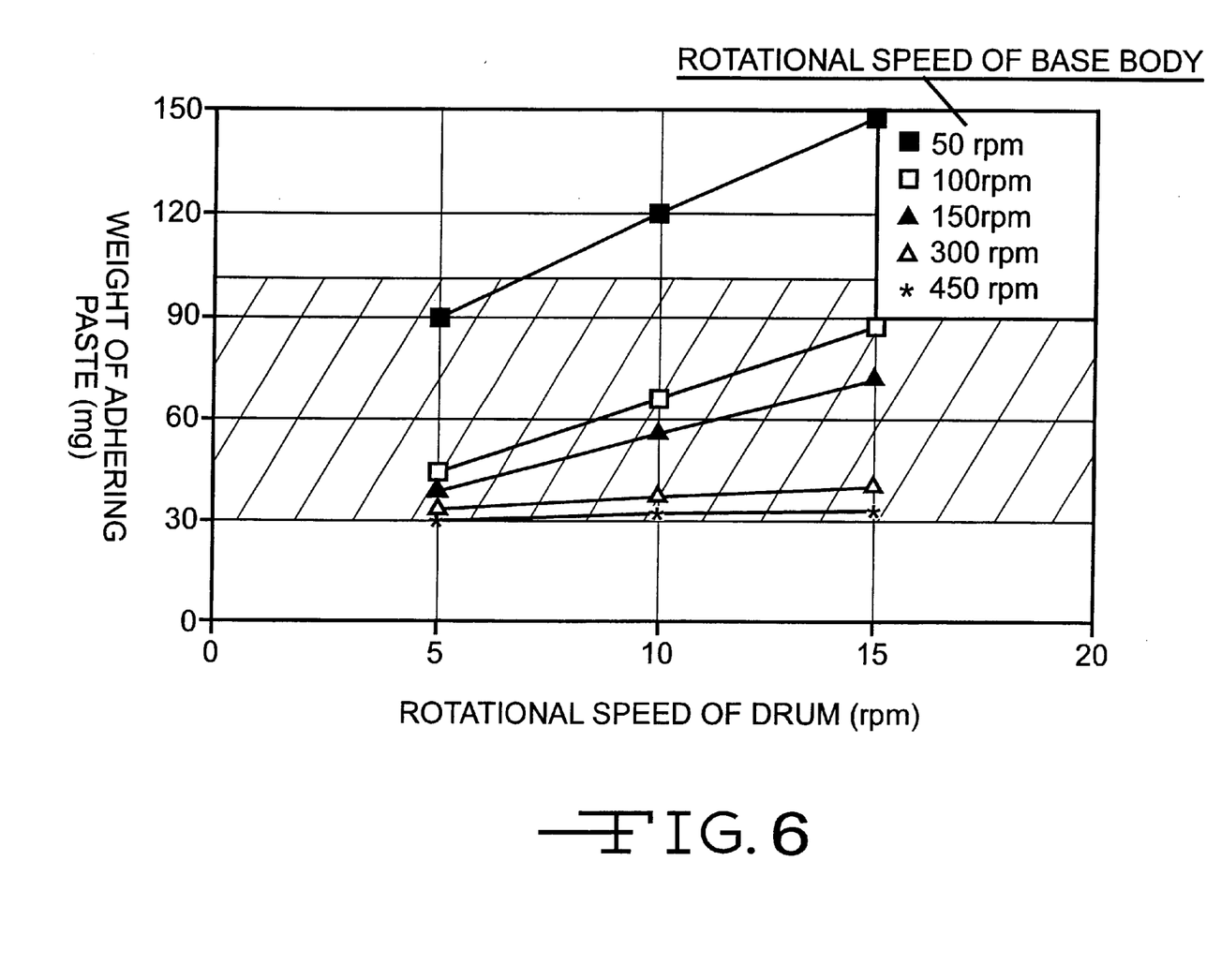
FIG. 6 presents a graph showing the relationship among the rotational speed of a drum, the rotational speed of a base body and the weight of adhering paste.

From the above test results, for the overflow coating application 1 of FIG. 6, the optimum rotational speed of the drum was judged to be 5 rpm to 15 rpm (equivalent to a moving speed of the paste of 2.4 cm/sec to 7.2 cm/sec at the position of contact between the paste and the base body) and the optimum rotational speed of the base body was judged to be 100 rpm to 700 rpm (equivalent to a moving speed of the base body of 3.4 cm/sec to 23.8 cm/sec at the position of contact between the paste and the base body).

The foregoing disclosure is the best mode devised by the inventors for practicing this invention. It is apparent, however, that apparatus and methods incorporating modifications and variations will be obvious to one skilled in the art of gas sensors and their manufacture. Inasmuch as the foregoing disclosure presents the best mode contemplated by the inventors for carrying out the invention and is intended to enable any person skilled in the pertinent art to practice this invention, it should not be construed to be limited thereby but should be construed to include such aforementioned obvious variations and be limited only by the spirit and scope of the following claims.

We claim:

1. A method for manufacturing a gas sensor element comprising the steps of: providing a substantially cylindrical base body made of an unfired solid electrolyte material; rotating such substantially cylindrical base body about an axis; providing a moving surface adjacent such rotating, substantially cylindrical base body; applying a paste including roughening particles of material substantially similar to that of such base body and having a viscosity of 500 CPS to 1600 CPS onto such base body in such a manner that such paste is brought into contact with such base body and is moved in a direction opposite to a moving direction of such base body at a position of contact between the paste and such base body moving surface, moving such moving surface in a direction opposite to a moving direction of a portion of such rotating base body adjacent such moving surface to bring such paste into contact with such rotating base body and firing such base body coated with such paste to form a plurality of projections in a single layer on such base body.

2. A method for manufacturing a gas sensor element according to claim 1 wherein the paste has a viscosity of 500 CPS to 1000 CPS.

3. A method for manufacturing a gas sensor element according to claim 1 wherein the weight of such paste adhering to such base body is 5.0 mg/cm$^2$ to 18.0 mg/cm$^2$.

4. A method for manufacturing a gas sensor element according to claim 3 wherein such paste has a viscosity of 500 CPS to 1000 CPS.

5. A method for manufacturing a gas sensor element according to claim 1 wherein such paste contains granules having a grain size of 20 μm to 100 μm and minute particles having a grain size smaller than that of such granules, and a mixture of such granules and such minute particles serves as such roughening particles.

6. A method for manufacturing a gas sensor element according to claim 5 wherein such paste contains such granules and such minute particles in a ratio of 80:20 to 20:80.

7. A method for manufacturing a gas sensor element according to claim 1 wherein such moving surface is an outer circumferential surface of a rotary drum rotating in the same direction as such base body, whereby such paste is present in a predetermined thickness on such drum.

8. A method for manufacturing a gas sensor element according to claim 7 wherein such paste has a viscosity of 500 CPS to 1000 CPS.

9. A method for manufacturing a gas sensor element according to claim 7 wherein the weight of such paste adhering to such base body is 5.0 mg/cm$^2$ to 18.0 mg/cm$^2$.

10. A method for manufacturing a gas sensor element according to claim 8 wherein such paste has a viscosity of 500 CPS to 1000 CPS.

11. A method for manufacturing a gas sensor element according to claim 7 wherein such paste contains granules having a grain size of 20 μm to 100 μm and minute particles having a grain size smaller than that of such granules, and a mixture of such granules and such minute particles serves as such roughening particles.

12. A method for manufacturing a gas sensor element according to claim 11 wherein such paste contains such granules and such minute particles in a ratio of 80:20 to 20:80.

13. A method for manufacturing a gas sensor element according to claim 7 wherein such base body is moved at a speed of 3.0 cm/sec to 24.0 cm/sec at a contact position so that such paste is moved at a speed of 2.0 cm/sec to 8.0 cm/sec at such contact position.

14. A method for manufacturing a gas sensor element according to claim 13 wherein such paste has a viscosity of 500 CPS to 1000 CPS.

15. A method for manufacturing a gas sensor element according of claim 13 wherein the weight of such paste adhering to such base body is 5.0 mg/cm² to 18.0 mg/cm².

16. A method for manufacturing a gas sensor element according to claim 15 wherein such paste has a viscosity of 500 CPS to 1000 CPS.

17. A method for manufacturing a gas sensor element according to claim 13 wherein such paste contains granules having a grain size of 20 μm to 100 μm and minute particles having a grain size smaller than that of such granules, and a mixture of such granules and such minute particles serves as such roughening particles.

18. A method for manufacturing a gas sensor element according to claim 17 wherein suchpaste contains such granules and such minute particles in a ratio of 80:20 to 20:80.

* * * * *

UNITED STATES PATENT AND TRADEMARK OFFICE
CERTIFICATE OF CORRECTION

PATENT NO.     : 6,544,586 B1
DATED          : April 8, 2003
INVENTOR(S)    : Takayoshi Atsumi et al.

It is certified that error appears in the above-identified patent and that said Letters Patent is hereby corrected as shown below:

Column 12,
Lines 9-13, delete "base body in such a manner that such paste is brought into contact with such base body and is moved in a direction opposite to a moving direction of such base body at a position of contact between the paste and such base body".

Column 14,
Line 4, delete "suchpaste" and substitute -- such paste -- in its place.

Signed and Sealed this

Thirtieth Day of September, 2003

JAMES E. ROGAN
*Director of the United States Patent and Trademark Office*